US009884030B2

(12) United States Patent
Isoda et al.

(10) Patent No.: US 9,884,030 B2
(45) Date of Patent: *Feb. 6, 2018

(54) PATCH BACKING FOR WATER-BASED PASTY PREPARATION

(75) Inventors: Hideo Isoda, Otsu (JP); Hiroyuki Sakamoto, Otsu (JP); Takashi Koida, Osaka (JP); Hiroyasu Sakaguchi, Osaka (JP); Sadanobu Shirai, Higashikagawa (JP); Masahiro Inazuki, Higashikagawa (JP); Miho Ishigure, Higashikagawa (JP)

(73) Assignees: TOYOBO CO., LTD., Osaka-shi, Osaka (JP); TEIKOKU SEIYAKU CO., LTD., Higashikagawa-shi, Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/809,549

(22) PCT Filed: Jul. 11, 2011

(86) PCT No.: PCT/JP2011/065763
§ 371 (c)(1),
(2), (4) Date: Mar. 11, 2013

(87) PCT Pub. No.: WO2012/008396
PCT Pub. Date: Jan. 19, 2012

(65) Prior Publication Data
US 2013/0164495 A1 Jun. 27, 2013

(30) Foreign Application Priority Data
Jul. 12, 2010 (JP) .................. 2010-157993

(51) Int. Cl.
*A61K 9/70* (2006.01)
*B32B 3/26* (2006.01)
*B32B 5/22* (2006.01)

(52) U.S. Cl.
CPC ............ *A61K 9/703* (2013.01); *A61K 9/70* (2013.01); *Y10T 428/24322* (2015.01)

(58) Field of Classification Search
CPC .......... A61K 9/70; A61K 9/702; A61K 9/703; A61K 9/7023–9/7092; B32B 3/266; B32B 5/022; B32B 9/045; B32B 27/32; B32B 33/00; B32B 2556/00; B32B 2535/00; B32B 2250/03; B32B 2307/726; B32B 2250/242; B32B 2250/40; B32B 2262/0253; B32B 2305/20; B32B 2307/51; B33B 27/12; A61M 35/00; A61F 13/0203; A61F 2013/00863; A61F 2013/00582; A61F 2013/00361; A61F 2013/00089; A61F 2013/00021; A61F 2013/00029; A61F 2013/00046; Y10T 428/2495; Y10T 428/24967

USPC ................ 428/137, 138; 604/304, 307, 308; 424/443, 445, 446; 442/381, 392, 398
See application file for complete search history.

(56) References Cited

U.S. PATENT DOCUMENTS

| | | | |
|---|---|---|---|
| 5,336,210 A | 8/1994 | Hidaka et al. | |
| 5,465,735 A | 11/1995 | Patel | |
| 5,935,682 A * | 8/1999 | Wallstrom | A61F 13/15707 428/137 |
| 6,210,704 B1 * | 4/2001 | Sasaki | A61F 13/02 424/443 |
| 6,903,243 B1 * | 6/2005 | Burton | 602/41 |
| 7,078,089 B2 * | 7/2006 | Ellis | D04H 1/559 156/163 |
| 2008/0269660 A1 | 10/2008 | Sigurjonsson et al. | |
| 2008/0287027 A1 * | 11/2008 | Suzuki | A61F 13/49009 442/416 |
| 2010/0076387 A1 | 3/2010 | Weimann et al. | |

(Continued)

FOREIGN PATENT DOCUMENTS

| | | |
|---|---|---|
| CN | 101094662 A | 12/2007 |
| EP | 0 484 543 A1 | 5/1992 |

(Continued)

OTHER PUBLICATIONS

Translation of the International Preliminary Report on Patentability (PCT/ISA/237) (5 pages), (PCT/IB/373) (1 page) of International Application No. PCT/JP2011/065763 dated Feb. 21, 2013 (Form PCT/IB/338) (1 page).

(Continued)

*Primary Examiner* — Joanna Pleszczynska
(74) *Attorney, Agent, or Firm* — Westerman, Hattori, Daniels & Adrian, LLP

(57) ABSTRACT

The present invention relates to a backing for a water-based patch consisting of the following constituents, wherein the backing is excellent in pasty preparation retention and moisture retention, improves the persistence of drug efficacy by inhibiting the sublimation of the drug, gives neither restrained feeling nor rough feeling due to a thin thickness and an excellent elasticity, controls the moisture permeability, gives almost no sticky feeling and thereby gives an excellent feeling in application. A patch backing for a water-based pasty preparation consisting of a laminate, wherein the laminate consists of three layers, a film layer having through-holes is laminated between a nonwoven fabric layer A and a nonwoven fabric layer B, said film layer consists of a resin containing an olefin elastomer, the through-hole area per a hole is 0.02-0.18 $mm^2$, and the opening ratio of the through-hole is 1-10%.

14 Claims, No Drawings

(56) References Cited

U.S. PATENT DOCUMENTS

2013/0138057 A1 5/2013 Shirai et al.
2013/0164495 A1 6/2013 Isoda et al.

FOREIGN PATENT DOCUMENTS

| JP | 3-161435 | A | 7/1991 |
|---|---|---|---|
| JP | 06-116141 | A | 4/1994 |
| JP | 6-238784 | A | 8/1994 |
| JP | 8-217668 | A | 8/1996 |
| JP | 8-260328 | A | 10/1996 |
| JP | 9-208469 | A | 8/1997 |
| JP | 10-298065 | A | 11/1998 |
| JP | 11-246397 | A | 9/1999 |
| JP | 2000-143503 | A | 5/2000 |
| JP | 2003-053894 | A | 2/2003 |
| JP | 2004-049544 | A | 2/2004 |
| JP | 2005-314618 | A | 11/2005 |
| JP | 2007-31322 | A | 2/2007 |
| WO | 2006/070672 | A1 | 7/2006 |
| WO | 2009/082602 | A2 | 7/2009 |
| WO | 2012/008396 | A1 | 1/2012 |

OTHER PUBLICATIONS

International Search Report for PCT/JP2011/065763, dated Aug. 2, 2011.
Extended European Search Report (EESR) dated Nov. 28, 2013, for PCT/JP2011/065762, which corresponds to EP Application No. 11806725.5 and the related U.S. Appl. No. 13/807,427.
English Translation of the International Preliminary Report on Patentabililty for PCT/JP2011/065762, dated Feb. 21, 2013, including English Translation of Written Opinion of the International Searching Authority, dated Aug. 2, 2011.
International Search Report of PCT/JP2011/065762, dated Aug. 2, 2011.
Chinese Office Action dated Nov. 15, 2014, issued in Chinese Application No. 201180034426.3, which corresponds to related U.S. Appl. No. 13/807,427. (11 pages).
Office Action dated Feb. 17, 2015, issued in corresponding Japanese Patent Application 2011-152476, w/English machine translation (6 pages).
U.S. Office Action dated May 20, 2015, issued in related U.S. Appl. No. 13/807,427 (15 pages).
U.S. Office Action dated Sep. 30, 2014, issued in co-pending U.S. Appl. No. 13/807,427.
U.S. Office Action dated Dec. 3, 2015, issued in co-pending U.S. Appl. No. 13/807,427 (10 pages).
Office Action dated Sep. 29, 2016, issued in co-pending U.S. Appl. No. 13/807,427 (10 pages).
Office Action dated May 5, 2017, issued in co-pending U.S. Appl. No. 13/807,427 (10 pages; including returned Form PTO/SB/08).
Office Action dated Dec. 3, 2015, issued in co-pending U.S. Appl. No. 13/807,427 (11 pages; including returned Form PTO/SB/08).

* cited by examiner

PATCH BACKING FOR WATER-BASED PASTY PREPARATION

TECHNICAL FIELD

The present invention relates to a patch backing for a water-based pasty preparation having excellent properties. More specifically, the present invention provides a patch backing for a water-based pasty preparation, which is excellent in pasty preparation retention and moisture retention, improves the persistence of drug efficacy by inhibiting the sublimation of the drug in the pasty preparation, is excellent in elasticity, gives no sticky feeling, has a thin thickness, and thereby gives an excellent feeling in application.

BACKGROUND ART

Patent Document 1 describes a patch, in which a backing is prepared by laminating a nonwoven fabric on at least one surface of a microporous synthetic resin film and a water-containing adhesive layer is laminated on the film side of the backing. However, this patch is deficient in the elasticities of the synthetic resin film and the nonwoven fabric, and thus has a problem with the feeling in application.

Patent Document 2 describes a base fabric of a patch which consists of an elastic film consisting of a composition containing an olefin copolymer component and a thermoplastic elastomer component, and a composite elastic film wherein an elastic nonwoven fabric is laminated on at least one surface of the film. Patent Document 2 also describes that said elastic film may be perforated or porous. However, in Patent Document 2, an investigation about a pasty preparation is not performed, and thus an investigation about the opening ratio and the opening area per a hole of the elastic film are not performed at all, and said patch has problems with pasty preparation retention and moisture retention, and persistence of drug efficacy due to the sublimation of the drug when a water-based pasty preparation is used.

PRIOR ART DOCUMENTS

Patent Documents

Patent Document 1: Japanese Patent Publication A 2000-143503
Patent Document 2: Japanese Patent Publication A 2004-049544

SUMMARY OF THE INVENTION

Problems to be Solved by the Invention

The present invention is made to solve the above-mentioned problems in the prior art. Namely, the object of the present invention is to provide a patch backing for a water-based pasty preparation, wherein the backing is excellent in pasty preparation retention and moisture retention, improves the persistence of drug efficacy by inhibiting the sublimation of the drug in the pasty preparation, gives neither restrained feeling nor rough feeling due to a thin thickness and an excellent elasticity, controls the moisture permeability, gives almost no sticky feeling and thereby gives an excellent feeling in application.

Means for Solving the Problems

The present inventors have studied earnestly, and as a result, found that the above-mentioned problems can be solved by the following means, and completed the present invention.

Namely, the present invention consists of the following aspects.

1. A patch backing for a water-based pasty preparation consisting of a laminate, wherein the laminate consists of three layers in which a film layer having through-holes is laminated between a nonwoven fabric layer A and a nonwoven fabric layer B, said film layer consists of a resin containing an olefin elastomer, the through-hole area per a hole is 0.02-0.18 mm$^2$, and the opening ratio of the through-hole is 1-10%.
2. The patch backing for a water-based pasty preparation according to the above-mentioned 1, wherein the moisture permeability of the backing is 1000-5500 g/m$^2$·24 hours.
3. The patch backing for a water-based pasty preparation according to the above-mentioned 1 or 2, wherein the 50% stretch recovery ratio is 70%-100%, the basis weight is 50-140 g/m$^2$, and the thickness is 0.2-0.8 mm.
4. The patch backing for a water-based pasty preparation according to any one of the above-mentioned 1-3, wherein the nonwoven fabric layer A and the nonwoven fabric layer B consist of an olefin resin.
5. The patch backing for a water-based pasty preparation according to any one of the above-mentioned 1-3, wherein the nonwoven fabric layer A and the nonwoven fabric layer B consist of a resin containing an olefin elastomer.

Effect of the Invention

A patch backing for a water-based pasty preparation of the present invention (hereinafter also referred to as "patch backing") consisting of a laminate, wherein the laminate consists of three layers in which a film layer consisting of a composition containing an olefin elastomer is laminated between a nonwoven fabric layer A and a nonwoven fabric layer B, the film layer has through-holes in which the hole shapes are retained, and the opening ratio of the through-hole is 1-10%, does not result in the closure of the openings in spite of using an elastomer, lowers the dampness by retaining the moisture permeability, and has a large non-opening area in the film, and thus can be used in the preparation of a patch in which the rapid moisture evaporation is inhibited, the sublimation of a drug in the pasty preparation is inhibited, and the persistence of drug efficacy is excellent. Also, because of the excellent stretch recovery, the backing is excellent in followability to a skin stretch and contraction, and thus a patch having a lowered oppressive and restrained feeling can be prepared by the backing. Because the both surfaces of the patch backing consist of nonwoven fabric layers, a peeling of the pasty preparation does not easily occur due to the anchor effect of the fiber constituting the nonwoven fabric layer. Also, because the thickness of the patch backing can be thin, the rough feeling in application can be lowered. Therefore, a patch which gives an excellent feeling in application can be prepared by the patch backing. Furthermore, the present invention can provide a patch backing for a water-based pasty preparation which is excellent in pasty preparation retention and moisture retention, improves the persistence of drug efficacy by inhibiting the sublimation of the drug in the pasty preparation, is excellent in elasticity, gives almost no sticky feeling, has a thin thickness, and gives an excellent feeling in application.

By utilizing the above-mentioned properties, the backing of the present invention can be expected to contribute to the field of nonwoven fabric use as a patch backing which can be applied to the various drug uses such as the transdermal absorbing agent (bandage) etc.

BEST MODE FOR CARRYING OUT THE INVENTION

Hereinafter, the present invention is described in detail.

The present invention relates to a patch backing for a water-based pasty preparation consisting of a laminate, wherein the laminate consists of three layers in which a film layer having through-holes is laminated between a nonwoven fabric layer A and a nonwoven fabric layer B, and said film layer is a film consisting of a resin containing an olefin elastomer. Furthermore, the present invention relates to a patch backing for a water-based pasty preparation, wherein the olefin elastomer film has through-holes in which the hole shapes are retained.

In the present invention, in order to stably retain the patch shape and give an elasticity to the patch, the laminated film layer is required to consist of a resin containing an olefin elastomer which can stably retain the property of the drug in the pasty preparation and exert an elasticity.

Other resin component, for example, polyester resin, is not preferable because it may have a low chemical resistance in some cases depending on the drug contained in the pasty preparation and a poor shape stability causing a wrinkle etc. Also, although a styrene elastomer is useful, it was not used in the present invention in view of the risk of the contact of a styrene oligomer with a skin.

In the present invention, it is preferred that the fiber which constitutes the nonwoven fabric layer A and the nonwoven fabric layer B consists of an olefin resin in the light of shape stability, and it is more preferred that the fiber which constitutes the nonwoven fabric layer A and the nonwoven fabric layer B consists of a resin containing an olefin elastomer in the light of elasticity.

The olefin elastomer used in the present invention may be a random or block copolymer of α-olefin such as ethylene, propylene, 1-butene, 4-methyl-1-pentene, or 1-octene, which is low crystalline with the crystallinity less than 50% or amorphous, and has MFR in the range of 20-100 g/10 minutes, preferably 50-80 g/10 minutes. Specifically, it may be a random or block copolymer of α-olefin etc. such as ethylene•propylene random or block copolymer, ethylene•1-butene random or block copolymer, propylene•1-butene random or block copolymer, or ethylene•1-octene random or block copolymer. The olefin elastomer used in the present invention is preferably a block or random copolymer of α-olefin, and more preferably ethylene•1-octene block or random copolymer with both smoothness and elasticity.

The resin containing an olefin elastomer used in the present invention is a thermoplastic resin composition which contains the above-mentioned olefin elastomer in 5%-100% by weight. A commercially available resin consisting of such composition can be exemplified by MORETEC (ethylene-1-octene copolymer) from Prime Polymer Co., Ltd. etc.

The olefin resin used in the present invention is a thermoplastic resin in which olefin monomers or alkene monomers are polymerized and a copolymer thereof, and can be exemplified by, for example, polyethylene, polypropylene, polybutene, ethylene-α-olefin copolymer, propylene-α-olefin copolymer, or ethylene vinyl alcohol etc. A preferred olefin resin can be exemplified by polyethylene or ethylene-α-olefin copolymer, and a more preferred olefin resin can be exemplified by ethylene•1-octene copolymer etc.

In the present invention, an air-permeable nonwoven fabric is used as the constituent nonwoven fabric, especially, a nonwoven fabric consisting of an olefin resin is preferred, and a nonwoven fabric consisting of an olefin resin and having elasticity is more preferred. A commercially available elastic nonwoven fabric which meets such requirements can be exemplified by STRAFLEX U type (an olefin long-fiber elastic nonwoven fabric) from Idemitsu Unitech Co. Ltd. etc.

In the patch backing for a water-based pasty preparation of the present invention, the film layer having through-holes is laminated on the nonwoven fabric layer A, then the nonwoven fabric layer B is further laminated on the film layer side to prepare a laminate consisting of three layers in which said film layer is a film layer consisting of a resin containing an olefin elastomer, or a laminate in which the nonwoven fabric layer A and the film layer consisting of a resin containing an olefin elastomer (hereinafter also referred to as "elastomer film layer") are laminated has through-holes in which the hole shapes are retained, and the nonwoven fabric layer B is further laminated on the film layer side.

In the present invention, it is necessary that the structure in which the nonwoven fabric layer A and the elastomer film layer are laminated has through-holes in which the hole shapes are retained.

It is not preferable to open the through-holes in the nonwoven fabric layer A and the elastomer film layer by a mechanical method such as a needle punch, because the opening shapes can not be maintained due to the elasticity of the elastomer film layer, then the openings close, the opening effects decrease, and thus the moisture permeability decreases.

In the present invention, by forming the openings with melting method and retaining the hole shapes of the openings, the hole shapes of the openings of the through-holes can be retained even after the shapes are changed by a stretch or a contraction, a high moisture permeability can be maintained, thereby the moisture caused by sweating from a skin can be released, and thus damp feeling (sticky feeling) can be lowered.

Also, although there was a risk of adverse effects that the openings may cause a high water evaporation by the moisture transmission, thereby the drug in the water-based pasty preparation may be sublimated, and the duration of drug efficacy may be shorten, such effects were not found. Namely, in the present invention, the through-hole area per a hole is 0.02-0.18 mm$^2$ and the opening ratio of the through-hole is adjusted to 1-10%, thereby the elastomer film layer exerts a barrier effect to inhibit the sublimation of the drug in the water-based pasty preparation, resulting in the improvement of the persistence of drug efficacy, as well as lowering of damp feeling (sticky feeling).

In the present invention, it is preferred that the nonwoven fabric layer A and the elastomer film layer are bonded into one, and then through-holes are formed from the film layer side. In the present invention, the opening ratio of the through-hole is preferably 1-10%, and more preferably 1-8%. When the opening ratio of the through-hole is more than 10%, the drug in the water-based pasty preparation is sublimated and the persistence of drug efficacy decreases, and when the opening ratio is less than 1%, the damp feeling (sticky feeling) can not be lowered. In the present invention, the through-holes pass from the film layer surface to the nonwoven fabric layer surface, and preferably the openings are formed so that the distribution of the openings is a substantially uniform distribution (which may also be a lattice arrangement, a staggered arrangement, or a random arrangement etc.), and a non-uniform distribution is not preferable because it causes a partial damp feeling (sticky feeling) and a non-uniform persistence of drug efficacy.

Also, the through-hole area per a hole is 0.02-0.18 mm$^2$, and preferably 0.05-0.17 mm$^2$. When the area is less than 0.02 mm$^2$, the moisture permeability ratio may decrease in some cases, and when the area is greater than 0.18 mm$^2$, an exudation of the water-based pasty preparation occurs.

It is preferred that the moisture permeability of the patch backing is adjusted to the range of 1000-5500 g/m$^2$·24 hours. When the moisture permeability is less than 1000 g/m$^2$·24 hours, a problem of damp feeling (sticky feeling) may occur in some cases, and when the moisture permeability is greater than 5000 g/m$^2$·24 hours, a problem in the persistence of drug efficacy may occur in some cases. The moisture permeability of the patch backing of the present invention is preferably 2000-4500 g/m$^2$·24 hours, and more preferably 2500-4000 g/m$^2$·24 hours.

In the patch backing of the present invention, the laminated structure is formed in which the nonwoven fabric layer B having no opening is further laminated on the elastomer film layer side of the film laminate having through-holes.

If the elastomer film layer surfaces are exposed, the problem is that an applied patch is easily caught by clothes due to the tack property of the elastomer, and easily peeled by contacting with clothes.

Laminating the nonwoven fabric having no opening is necessary to give the patch an abrasion resistance and a smoothing effect when contacting with clothes. Furthermore, the nonwoven fabric having no opening also has a function to adjust the moisture permeability of the film layer having through-holes or the other nonwoven fabric layer/film elastomer layer laminate.

Preferably, in the patch backing of the present invention, the 50% stretch recovery ratio is 70%-100%, the basis weight is 50-140 g/m$^2$, and the thickness is 0.2-0.8 mm.

When the 50% stretch recovery ratio of the patch backing is less than 70%, the followability to a skin stretch and contraction becomes low, and an oppressive feeling or a peeling may occur in some cases. In the present invention, the stretch recovery ratio is preferably 80%-100%, and more preferably 85%-100%. In one embodiment of the present invention, the elasticity of the patch backing can be more improved by using an olefin elastomer component in the fiber constituting the nonwoven fabric layer.

As the basis weight becomes lower, the patch backing becomes lighter. However, the basis weight less than 50 g/m$^2$ may result in an insufficient reinforcing effect, a damage, and a difficulty in shape retention in some cases. Also, in case a water-based pasty preparation is used, an exudation may occur in some cases. The basis weight greater than 150 g/m$^2$ may result in a rough feeling or a restrained feeling in some cases, and thus can not be recommended. In the patch backing of the present invention, the basis weight is more preferably 60-120 g/m$^2$, and still more preferably 80-110 g/m$^2$.

When the thickness of the patch backing is less than 0.1 mm, the anchor effect in the water-based pasty preparation becomes insufficient and the pasty preparation may peel in some cases. When the thickness is greater than 1.0 mm, a rough feeling occurs in some cases. The thickness of the patch backing of the present invention is more preferably 0.2-0.6 mm, and still more preferably 0.3-0.5 mm. Such a thin patch backing exerts effects that the thickness of the patch also becomes thin and the uncomfortable feeling in application decreases.

The nonwoven fabric layer which constitutes the patch backing of the present invention is not limited, and is preferably a long-fiber nonwoven fabric, i.e., a nonwoven fabric having a high strength, and more preferably, a spun-bond nonwoven fabric which is highly productive and excellent in shape retention can be recommended. It is preferred that the fineness of the fiber which constitutes the nonwoven fabric layer is 0.5 dtex-10 dtex in which the flexibility and the compact reinforcement can be maintained. The fineness less than 0.5 dtex easily results in a thread breakage, and the fineness greater than 10 dtex results in a decrease in compactness and flexibility. The fineness is preferably 1.0 dtex-8 dtex, and more preferably 1.5 dtex-6 dtex.

The nonwoven fabric layer A and the nonwoven fabric layer B may be the same in the constituents, and may be different in the basis weight, the thickness, the fineness or the composition of the constituent fiber. However, the basis weight less than 15 g/m$^2$ may result in an exudation in some cases. Accordingly, it is preferred that the nonwoven fabric layers having the basis weight of 15-80 g/m$^2$ are appropriately selected and combined to obtain the patch backing having the basis weight of 50-140 g/m$^2$. Although it is preferable that the fiber which constitutes the nonwoven fabric layers is selected so that the nonwoven fabric layer A and the nonwoven fabric layer B consist of a resin containing an olefin elastomer, it is also acceptable that one nonwoven fabric layer consists of a resin containing no olefin elastomer, and the other nonwoven fabric layer consists of a resin containing an olefin elastomer. In any case, it is preferable that the fiber which constitutes the nonwoven fabric layers is selected so that the elasticity of the patch backing meets the preferred stretch recovery ratio of the present invention. As an embodiment of the present invention, while it is preferred that the nonwoven fabric layer A and the nonwoven fabric layer B have the same constituents in the light of productivity, it is preferred that the basis weight of at least the nonwoven fabric layer B is 1-2 times higher than the basis weight of the nonwoven fabric layer A in the light of coatability.

Although the mechanical properties of the patch backing of the present invention are not limited, it is a preferable embodiment that the tensile strength required for shape retention of the fiber structure is at least 10 N/25 mm or more, and preferably 15 N/25 mm or more.

Although an example of a process for preparing the patch backing of the present invention is described below, the present invention is not intended to be limited to it by any means.

A process for preparation of the patch backing of the present invention using the most preferred olefin resin as an example is described below.

A resin in which polyethylene and ethylene-1-octene copolymer are mixed as main ingredients depending on the desired elasticity required for the nonwoven fabric is spun in a normal melting spinning machine at the spinning temperature (180)° C. The discharge rate is set depending on the setting tractive speed in order to obtain the desired fineness. For example, if a fiber of 2 dtex is desired to be obtained and the spinning speed by traction is set to 2000 m/min, the discharge is performed in the discharge rate of 0.4 g/min per a hole.

The spun and discharged line of thread is cooled by a cooling air at about 10 cm just below a nozzle, pulled and thinned by a traction jet placed below to be solidified, received by a net or a drum with an aspirator just before the elastic resilience generates, and laminated to become a desired basis weight (the recommended basis weight of the nonwoven fabric is 20-60 g/m$^2$). Continuously, the web is pre-pressed so as not to disassemble and thus the handling ability is ensured. Then, the nonwoven fabric is reeled, or embossed if necessary. Because the nonwoven fabric is a soft material, an embossing by a dot pressing at low temperature is recommended. The nonwoven fabric B having a desired basis weight can also be obtained in the same way.

Then, an ethylene-α-olefin resin is laminated on the obtained nonwoven fabric by a conventional method. The thickness of the laminate film is not limited. However, when the thickness is less than 5 μm, the problem is that a homogeneous lamination becomes difficult and the film easily becomes damaged in the manufacturing process. When the thickness is greater than 50 μm, the elasticity of the patch backing depends on the elasticity of the film alone, resulting in a restrained feeling in some cases. Accordingly, in the present invention, the thickness of the elastomer film layer is preferably 5 μm or more to 50 μm or less, and more preferably 10-30 μm. The thickness of the elastomer film layer is adjusted by the processing speed and the discharge rate of the resin from a die and thus an elastomer film layer having a desired thickness can be laminated.

Then, in the present invention, through-holes in which the opening shapes can be retained are formed in the nonwoven fabric laminate in which the elastomer film layer is laminated. As a method for forming the through-holes in which the hole shapes can be retained, a hot needle processing is preferred. If the openings are formed by a needle punch or a waterjet, then the openings are opened by stretching the elastomer film, and thus the holes may be closed by the contraction after opening in some cases. Therefore, in the present invention, a hot needle processing is recommended, which can open the openings by melting and thereby the hole shapes can be retained. The holes having desired hole diameters and pitches can be formed by a conventional hot needle processing. In the present invention, the opening ratio of the through-hole is 1-10%, and the through-hole area per a hole is in the range of 0.02-0.18 mm². It is preferred that the opening ratio and the through-hole area are adjusted so that the patch backing having the three-layer laminate in which the nonwoven fabric layer B is laminated and bonded has the moisture permeability in the range of 1000-5500 g/m²·24 hours. Also, it is preferred that the opening by a hot needle processing is performed from the film side.

Then, the nonwoven fabric layer B is laminated and bonded on the elastomer film layer side of the laminate of the nonwoven fabric layer A and the elastomer film layer having the through-holes.

Although the nonwoven fabric layer B is not limited as long as it meets the condition of the elasticity, the moisture permeability, and the abrasion resistance required for the patch backing, and the thickness and basis weight required for weight saving, it is preferred that the nonwoven fabric layer B is the same as the nonwoven fabric layer A, or has a higher basis weight than the nonwoven fabric layer A in the light of abrasion resistance and coatability.

Although the bonding method is not limited, a bonding method by applying an adhesive agent (α-olefin series, acrylic resin series, or polypropylene series etc. can be used) is recommended as a method which does not result in a deformation of the elastomer film layer. The method for applying an adhesive agent may be a spraying method or a gravure transfer method etc. It is preferred that the application amount of an adhesive agent is low as long as the nonwoven fabric layer B is homogeneously bonded to the elastomer film layer and is not peeled by an external force, and the amount is preferably 1-10 g/m², and more preferably 2-5 g/m².

Thus, by means of using a conventional method, the nonwoven fabric layer B is laminated and bonded to the two-layer laminate of the nonwoven fabric layer A/elastomer film layer, and reeled to obtain the patch backing having the three-layer laminate of the present invention.

Then, a water-based pasty preparation is spread on a liner film, laminated and bonded to the above-obtained patch backing, cut, sealed, and aged to obtain various patches.

The patch for a water-based pasty preparation using the patch backing of the present invention is excellent in pasty preparation retention and moisture retention, improves the persistence of drug efficacy by inhibiting the sublimation of the drug, has an excellent elasticity, gives less sticky feeling, has a thin thickness and thereby gives an excellent feeling in application.

EXAMPLES

Although the present invention is specifically explained by Examples below, the present invention is not intended to be limited to them by any means.

Also, in the present invention, the evaluations described in Examples are performed by the following methods.

<Single-Fiber Fineness>

Samples having the size of 1 cm² were taken from randomly-selected 10 places on the nonwoven fabric surface, each of them was measured (n=20) to obtain the total average value φa of the fiber diameter, each specific gravity of the fiber was measured (n=3) to obtain the average value ρa, and the fineness (dtex) was calculated by the following formula.

$$\text{Fineness (dtex)} = \pi \times \varphi a2 \times \rho a/400$$

<Basis Weight>

Weight per unit area (g/m²) measured according to JIS L-1096 (2000).

<Thickness>

Thickness (mm) measured in the load of 0.196 N according to JIS L-1096 (2000).

<Through-Hole>

A surface observation was performed from the nonwoven fabric layer A side of the patch backing, then a through-hole was defined as the state that the nonwoven fabric layer B surface could be seen, and an SEM photography at 2-10 times magnification was taken to obtain the opening area (S) using the following calculation. Three observation points were randomly selected, a photo in the range of 1 cm² of each point was taken, and the number of through-holes (n) and the individual area (Si) in the range of 1 cm² were determined. The average value (Sj) of the through-hole area (Si) was determined at each measurement point, and the average value of the Sj was defined as the opening area.

$$\text{Opening area (mm}^2\text{)} = (1/3)\Sigma(Sj) = (1/3)\Sigma((1/n)\Sigma(Si))$$

The opening ratio was expressed as the average value of the opening ratio calculated from the total of the above-mentioned individual through-hole area (Si) at each measurement point.

Opening ratio at each measurement point=Σ(Si)

<50% Stretch Recovery Ratio>

The stretch modulus determined according to JIS L-1096 8.13.2, except that the sample width was set to 25 mm, the sample length was set to 100 mm, the tensile speed was set to 100%, and the sample was stretched to 50%, was defined as the 50% stretch recovery ratio (%).

<Moisture Permeability>

The moisture permeability was measured according to JIS L-1099 (2006) 7.1 A method (calcium chloride method).

<Preparation of Patch>

A water-based pasty preparation ("(b) pasty preparation 2" described in Example 1 of Japanese Patent Publication A 2007-176854 and 3 parts by weight of methyl salicylate as a tracer were kneaded to prepare the pasty preparation) was spread on the peeling polypropylene film surface by a film applicator so that the thickness became 1000 μm, then the pasty preparation was laminated and bonded to the nonwoven fabric A surface of a cut patch backing, sealed into an aluminum vapor-deposited pack with a zipper, and aged at 40° C. for 24 hours to prepare a patch.

<Evaluation of Patch Appearance>

The prepared patch was taken out of the pack, visually observed, and the following evaluations were performed.
(1) Wrinkle: Observations about the generation of a wrinkle on the backing were performed and evaluations were performed as follows.
  No wrinkle: ●, Very few wrinkles: ▲, Observable wrinkles: ×
(2) Stretch or contraction of backing: Observations about a stretch or a contraction on the backing were performed and evaluations were performed as follows.
  No stretch or contraction: ●, Very few stretches or contractions: ▲, Observable stretches or contractions: ×
(3) Exudation: Observations about exudation of the moisture or the pasty preparation into the backing surface were performed and evaluations were performed as follows.
  No exudation: ●, Observable exudation: ×.

<Evaluation of Feeling in Application of Patch>

The patches were applied to 10 panelists on their knees and elbows for 12 hours, and then organoleptic evaluations and the following evaluations by visual judgments were performed.
(1) Sticky feeling (including damp feeling): Organoleptic evaluations about damp or sticky feeling in application were performed. Also, the rank of the evaluation was downgraded if one or more out of ten panelists pointed out a problem of (slightly) sticky feeling. The evaluations were performed as follows.
  Non-sticky: ●, Slightly sticky: ▲, Sticky: ×
(2) Feeling in application: Organoleptic evaluations about fit in application were performed. Also, the rank of the evaluation was downgraded if one or more out of ten panelists pointed out a problem of (slightly) bad fit. The evaluations were performed as follows.
  Excellent fit: ●, Slightly bad fit: ▲, Bad fit: ×
(3) Pasty preparation retention: Evaluations for the presence of a peeling or a burr in application were performed. Also, the rank of the evaluation was downgraded if one or more out of ten panelists pointed out a problem of peeling or burr. The evaluations were performed as follows.
  No peeling or burr: ●, Few burrs only: ▲, Observable burrs or peelings: ×
(4) Fuzz damage: The condition of the backing surface after application was visually judged, and the average value was rounded to perform evaluations. The evaluations were performed as follows.
  No fuzz: ●, Little fuzz: ▲, Observable fuzz: ×.

<Moisture Retention>

The initial weight of the patch (W0) and the weight of the patch after dried for 4 hours in a dry condition at 40° C. (Wi) were measured, then the amount of weight loss (ΔW) was calculated, the amount of loss was deemed as the amount of moisture, and the moisture retention rate (W) was calculated.

Moisture retention rate $(W) = \{1-(W0-Wi)/W0\} \times 100$ (%)

<Persistence of Drug Efficacy>

The applied patch was immediately peeled, and the remaining amount of methyl salicylate as the active ingredient in the pasty preparation was measured. In the measurement, the patch was immersed in ethanol, subjected to an ultrasonic vibration, eluted, and then subjected to a gas chromatography to perform a quantitative analysis. The remaining amount of methyl salicylate in the patch after applied for 12 hours was compared to an unapplied patch and evaluated as follows.

50% or more: ●, 30% or more: ▲, Less than 30%: ×

Example 1

On UN5050 from Idemitsu Unitech Co. Ltd. (a spunbond nonwoven fabric using an olefin elastomer resin, having the basis weight of 50 g/m², the thickness of 0.3 mm, and the fineness of 5 dtex) as the nonwoven fabric layer A was laminated a film of MORETEC 0218CN (ethylene-1-octene copolymer) from Prime Polymer Co., Ltd. having the thickness of 20 μm, and then a hot needle processing was performed from the elastomer film side by a needle having the diameter of 0.7 mm to form through-holes in which the hole shapes having the through-hole area per a hole of 0.05 mm² and the opening ratio of 1.4% were retained. Then, UN5040R (a spunbond nonwoven fabric using an olefin elastomer resin, having the basis weight of 45 g/m², and the thickness of 0.25 mm) from Idemitsu Unitech Co. Ltd. as the nonwoven fabric layer B was laminated and bonded to the elastomer film surface of the nonwoven fabric layer A/elastomer film laminate in which the through-holes were formed, using a conventional method, i.e., applying an adhesive agent by a spraying method in the amount of 5 g/m² to obtain a backing having the basis weight of 105 g/m², the thickness of 0.4 mm, 50% stretch recovery ratio of 92%, and the moisture permeability of 3500 g/m²·24 hours.

The performances of the obtained backing and the evaluation results of the patch using the backing are shown in Table 1.

The patch using the backing of Example 1 was a patch for a water-based pasty preparation which had an excellent elasticity and an excellent pasty preparation retention property, gave no sticky feeling and an excellent feeling in application, had also an excellent moisture retention property, and improved the persistence of drug efficacy by inhibiting the sublimation of the drug.

Example 2

The similar backing as Example 1 was prepared except that the through-hole area per a hole was 0.17 mm² and the opening ratio was 1.4% in the elastomer film of Example 1. The backing having the basis weight of 105 g/m², the thickness of 0.4 mm, the 50% stretch recovery ratio of 91%, and the moisture permeability of 5300 g/m²·24 hours was obtained.

The performances of the obtained backing and the evaluation results of the patch using the backing are shown in Table 1.

The patch using the backing of Example 2 was a patch for a water-based pasty preparation which had an excellent elasticity and an excellent pasty preparation retention property, gave no sticky feeling and an excellent feeling in application, had also an excellent moisture retention property, and improved the persistence of drug efficacy by inhibiting the sublimation of the drug.

Example 3

On U type 30 g/m² (a spunbond nonwoven fabric using an olefin elastomer resin, having the basis weight of 30 g/m², the thickness of 0.2 mm, and the fineness of 5 dtex) from Idemitsu Unitech Co. Ltd. as the nonwoven fabric layer A was laminated a film of MORETEC 0218CN (ethylene-1-octene copolymer) from Prime Polymer Co., Ltd. having the thickness of 15 μm, and then a hot needle processing was performed from the elastomer film side by a needle having the diameter of 0.7 mm to form through-holes in which the hole shapes having the through-hole area per a hole of 0.05 mm² and the opening ratio of 1.4% were retained. Then, U type 30 g/m² (a spunbond nonwoven fabric using an olefin elastomer resin, having the basis weight of 30 g/m², and the thickness of 0.2 mm) from Idemitsu Unitech Co. Ltd. as the nonwoven fabric layer B was laminated and bonded to the elastomer film surface of the nonwoven fabric layer A/elastomer film laminate in which the through-holes were formed, using a conventional method, i.e., applying an adhesive agent by a spraying method in the amount of 4 g/m² to obtain a backing.

The performances of the obtained backing and the evaluation results of the patch using the backing are shown in Table 1.

The patch using the backing of Example 3 was a patch for a water-based pasty preparation which had an excellent elasticity and an excellent pasty preparation retention property, gave no sticky feeling and an excellent feeling in application, had also an excellent moisture retention property, and improved the persistence of drug efficacy by inhibiting the sublimation of the drug.

Comparative Example 1

The patch backing was prepared in a similar method as Example 1 except that the hot needle processing was not performed.

The performances of the obtained patch backing and the evaluation results of the patch using the backing are shown in Table 1.

The moisture permeability of the patch backing in Comparative Example 1 was out of the prescribed range of the present invention, and thus the backing gave a sticky feeling and had a problem in feeling in application.

Comparative Example 2

The patch backing was prepared in a similar method as Example 2 except that the holes were opened by a needle punch processing in the pene number of 50 in place of the hot needle processing.

The performances of the obtained patch backing and the evaluation results of the patch using the backing are shown in Table 1.

The moisture permeability of the patch backing in Comparative Example 2 was out of the prescribed range of the present invention, and thus the backing gave a sticky feeling and had a problem in feeling in application.

Comparative Example 3

The patch backing was prepared in a similar method as Example 2 except that Pelprene P30A, which is a polyester material, from Toyo Boseki Co. Ltd. was used as the laminate film material, and the thickness of the laminate film was 20 μm.

The performances of the obtained patch backing and the evaluation results of the patch using the backing are shown in Table 1.

The material of the laminate film of the patch backing in Comparative Example 3 was not an olefin material, which is a constituent feature of the present invention, and thus had problems that minor wrinkles occurred (which might be due to the swelling by the absorption of the pasty preparation drug) and the commercial value became worse.

Comparative Example 4

The patch backing was prepared by similarly laminating and bonding as Example 3 except that U type 30 g/m² from Idemitsu Unitech Co. Ltd. which was used in Example 3 was used as the nonwoven fabric layer A and the nonwoven fabric layer B, the film lamination and the hot needle processing were not performed, and laminate-bonding was performed by applying an adhesive agent in the amount of 10 g/m².

The performances of the obtained patch backing and the evaluation results of the patch using the backing are shown in Table 1.

Regarding the patch backing in Comparative Example 4, the film lamination was not performed on the nonwoven fabric layer A, thus the backing did not meet the constituent features of the present invention, and had problems that exudation of the drug slightly occurred, and the moisture retention property and the persistence of drug efficacy became worse.

Comparative Example 5

The backing, which was prepared by performing only a lamination on the nonwoven fabric layer A obtained in Example 1, was used as the patch backing, and the film side and the pasty preparation were bonded to prepare the patch. The results are shown in Table 1.

The patch backing in Comparative Example 5 was insufficient in the bonding power between the film and the pasty preparation, and had problems of a pasty preparation peeling and a sticky feeling.

Comparative Example 6

The backing, which was prepared by performing only a lamination on the nonwoven fabric layer A obtained in Example 1 and a hole-opening by a hot needle processing, was used as the patch backing, and the film side and the pasty preparation were bonded to prepare the patch. The results are shown in Table 1.

Although the patch backing in Comparative Example 6 lowered a sticky feeling, it was insufficient in the affinity between the film and the pasty preparation, and had a problem of a pasty preparation peeling.

Comparative Example 7

The backing, which was prepared by performing only a lamination on the nonwoven fabric layer A obtained in Example 1, was used as the patch backing, and the nonwoven fabric A side and the pasty preparation were bonded to prepare the patch. The results are shown in Table 1.

Although the patch backing in Comparative Example 7 was excellent in bonding between the nonwoven fabric layer A and the pasty preparation, the frictional resistance of the laminate film functioned as a binding force in contact with clothes, and thus easily generated a rough feeling and a burr, and also had a problem of a sticky feeling.

Comparative Example 8

The backing, which was prepared by performing only a lamination on the nonwoven fabric layer A obtained in Example 1 and a hole-opening by a hot needle processing, was used as the patch backing, and the nonwoven fabric layer A side and the pasty preparation were bonded to prepare the patch. The results are shown in Table 1.

Although the patch backing in Comparative Example 8 lowered a sticky feeling, the frictional resistance of the laminate film functioned as a binding force in contact with clothes, and thus had a problem of easily generating a rough feeling and a burr.

Comparative Example 9

The patch backing was prepared in a similar method as Example 1 except that NOVATEC FL02 (polypropylene) having the melt index of 2.0 from Japan Polypropylene Corporation was used as the material for the laminate film in place of ethylene-1-octene copolymer and the film lamination in the thickness of 20 μm was performed.

The performances of the obtained patch backing and the evaluation results of the patch using the backing are shown in Table 1.

The patch backing in Comparative Example 9 was prepared by using polypropylene as the laminate film which was a nonelastomer, thus had problems of a poor elasticity, a rough feeling in application and a slack on the nonwoven fabric resulting in a partially peeling of the film etc.

Comparative Example 10

The backing was prepared in a similar method as Example 3 except that the hot needle processing was performed by a needle having the diameter of 0.05 mm to form the through-holes having the through-hole area per a hole of 0.05 $mm^2$ and the opening ratio of 0.5%.

The performances of the obtained backing and the evaluation results of the patch using the backing are shown in Table 1.

Although the patch backing in Comparative Example 11 was excellent in elasticity, the hole formed was small and had a low opening ratio, thus the backing had problems of a slightly poor moisture permeability and a sticky feeling.

Comparative Example 11

The backing was prepared in a similar method as Example 3 except that the hot needle processing was performed by a needle having the diameter of 3.0 mm to form the through-holes having the through-hole area per a hole of 3.0 $mm^2$ and the opening ratio of 15.0%.

The performances of the obtained backing and the evaluation results of the patch using the backing are shown in Table 1.

Although the patch backing in Comparative Example 12 was excellent in elasticity, the hole formed was large and had a high opening ratio, thus the backing had problems of a too high moisture permeability resulting in a slightly poor moisture retention property, a slightly poor persistence of drug efficacy, and a little exudation of the drug.

Comparative Example 12

The backing was prepared in a similar method as Example 1 except that the hot needle processing was performed by a needle having the diameter of 0.8 mm to form the through-holes having the through-hole area per a hole of 0.2 $mm^2$ and the opening ratio of 1.4%.

The performances of the obtained backing and the evaluation results of the patch using the backing are shown in Table 1.

Although the patch backing in Comparative Example 12 was excellent in elasticity, the hole formed was large, thus the backing had problems of a high moisture permeability resulting in a slightly poor moisture retention property, a slightly poor persistence of drug efficacy, and a little exudation of the drug.

Example 4

The backing was prepared in a similar method as Example 3 except that a spunbond nonwoven fabric having the basis weight of 30 $g/m^2$, the thickness of 0.2 mm, and the fineness of 6 dtex which was prepared by a conventional melt-spinning of MORETEC 0218CN (ethylene-1-octene copolymer) from Prime Polymer Co., Ltd. was used as the nonwoven fabric layer A and the nonwoven fabric layer B, then a film having the thickness of 15 μm was laminated on the nonwoven fabric layer A using Milastomer 5030N (a blend resin of polypropylene/ethylene•propylene•diene elastomer) from Mitsui Chemicals, Inc., and the hot needle processing was performed by a needle having the diameter of 0.8 mm to form the through-holes in which the hole shapes having the through-hole area per a hole of 0.1 $mm^2$ and the opening ratio of 2.8% were retained. The properties of the backing and evaluation results of the patch using the backing are shown in Table 1.

The patch backing in Example 4 had an excellent pasty preparation retention property and an excellent elasticity, gave no sticky feeling and an excellent feeling in application, had an excellent moisture retention property, and also showed an excellent persistence of drug efficacy by inhibiting the sublimation of the drug.

Example 5

The patch backing was prepared in a similar method as Example 1 except that STRAFLEX UN5100 (an olefin elastic spunbond nonwoven fabric having the basis weight of 100 $g/m^2$, the thickness of 0.5 mm, and the fineness of 5 dtex) from Idemitsu Unitech Co. Ltd. was used as the nonwoven fabric layer A and the nonwoven fabric layer B. The properties of the backing and the evaluation results of the patch using the backing are shown in Table 1.

Although the patch backing in Example 5 was excellent in elasticity of the nonwoven fabric, the thickness of the patch backing was too thick, thus the stress required for following a skin stretch and contraction became high resulting in a slightly more rough feeling in application compared to Examples 1-4.

Example 6

The backing was prepared in a similar method as Example 3 except that a melt blown nonwoven fabric having the basis weight of 10 g/m², the thickness of 0.1 mm, and the fineness of 0.4 dtex which was prepared by a conventional melt blowing of MORETEC 0218CN (ethylene-1-octene copolymer) from Prime Polymer Co., Ltd. was used as the nonwoven fabric layer A and the nonwoven fabric layer B, then a film having the thickness of 15 μm was laminated on the nonwoven fabric layer A using Milastomer 5030N (a blend resin of polypropylene/ethylene•propylene•diene elastomer) from Mitsui Chemicals, Inc., and a hot needle processing was performed by a needle having the diameter of 0.8 mm to form the through-holes in which the hole shapes having the through-hole area per a hole of 0.1 mm² and the opening ratio of 2.8% were retained. The properties of the backing and the evaluation results of the patch using the backing are shown in Table 1.

Although the patch backing in Example 6 was excellent in elasticity, the nonwoven fabric layer A and the nonwoven fabric layer B had the low basis weight and the thin thickness, thus the backing generated slightly more exudation of pasty preparation drug or water when used for a water-based pasty preparation compared to Examples 1-4.

Example 7

The patch backing was prepared in a similar method as Example 1 except that ecule 3201A (a polyester spunbond having the basis weight of 20 g/m² and the thickness of 0.15 mm) from Toyo Boseki Co. Ltd. was used as the nonwoven fabric layer A and the nonwoven fabric layer B.

The performances of the obtained patch backing and the evaluation results of the patch using the backing are shown in Table 1.

Although the patch for a water-based pasty preparation in Example 7 showed a slightly weaker elasticity compared to Examples 1-4, it showed an excellent pasty preparation retention, gave no sticky feeling and an excellent feeling in application, also showed an excellent moisture retention, and improved the persistence of drug efficacy by inhibiting the sublimation of the drug.

Example 8

The patch backing was prepared in a similar method as Example 1 except that SYNTEX (a polypropylene spunbond having the basis weight of 30 g/m² and the thickness of 0.3 mm) from Mitsui Chemicals, Inc. was used as the nonwoven fabric layer A and the nonwoven fabric layer B.

The performances of the obtained patch backing and the evaluation results of the patch using the backing are shown in Table 1.

Although the patch for a water-based pasty preparation in Example 8 showed a slightly weaker elasticity compared to Examples 1-4, it showed an excellent pasty preparation retention, gave no sticky feeling and an excellent feeling in application, also showed an excellent moisture retention, and improved the persistence of drug efficacy by inhibiting the sublimation of the drug.

TABLE 1

| | | | Example 1 | Example 2 |
|---|---|---|---|---|
| Nonwoven fabric layer A | Composition | | Polyethylene elastomer | Polyethylene elastomer |
| | Basis weight | g/m² | | |
| | Thickness | mm | | |
| | Fiber fineness | dtex | | |
| Laminate film | Composition | | Ethylene-1-ocetene | Ethylene-1-ocetene |
| | Thickness | μm | 20 | 20 |
| | Laminate-bonding | | Laminate | Laminate |
| Opening | Method | | Hot needle processing | Hot needle processing |
| | Through-hole | | Effective opening | Effective opening |
| | Opening area | mm² | 0.05 | 0.17 |
| | Opening ratio | % | 1.4 | 1.4 |
| | Hole arrangement | | Lattice | Lattice |
| Nonwoven fabric layer B | Composition | | Polyethylene elastomer | Polyethylene elastomer |
| | Basis weight | g/m² | 45 | 45 |
| | Thickness | mm | 0.25 | 0.25 |
| | Fiber fineness | dtex | 5 | 5 |
| Laminate-bonding of B | Bonding surface | | Laminate film surface | Laminate film surface |
| | Adhesive agent | | Spray bonding | Spray bonding |
| | Amount of adhesive agent | g/m² | 5 | 5 |
| Patch backing | Basis weight | g/m² | 120 | 120 |
| | Thickness | mm | 0.58 | 0.58 |
| | 50% stretch recovery (Machine Direction) | % | 92 | 91 |
| | 50% stretch recovery (Transverse Direction) | % | 91 | 91 |
| | Moisture permeability | g/m²/24 hr | 3500 | 5300 |
| Pasty preparation-laminated surface | | | Nonwoven fabric A surface | Nonwoven fabric A surface |
| Patch appearance | Wrinkle | | • | • |
| | Stretch or contraction of backing | | • | • |
| | Exudation | | • | • |
| Evaluation of patch application | Sticky feeling (including damp feeling) | | • | • |
| | Feeling in application | | • | • |
| | Pasty preparation retention | | • | • |
| | Fuzz damage | | • | • |
| Retention of patch function | Moisture retention | % | 55 | 35 |
| | Persistence of drug efficacy | | • | • |

TABLE 1-continued

|  |  |  | Example 3 | Example 4 | Example 5 |
|---|---|---|---|---|---|
| Nonwoven fabric layer A | Composition |  | Polyethylene elastomer | Polyethylene elastomer | Ethylene-1-octene |
|  | Basis weight | g/m² | 30 | 100 | 10 |
|  | Thickness | mm | 0.2 | 0.5 | 0.1 |
|  | Fiber fineness | dtex | 5 | 5 | 0.4 |
| Laminate film | Composition |  | Ethylene-1-octene | Ethylene-1-octene | PP/EPDM |
|  | Thickness | μm | 15 | 20 | 15 |
|  | Laminate-bonding |  | Laminate | Laminate | Laminate |
| Opening | Method |  | Hot needle processing | Hot needle processing | Hot needle processing |
|  | Through-hole |  | Effective opening | Effective opening | Effective opening |
|  | Opening area | mm² | 0.05 | 0.05 | 0.1 |
|  | Opening ratio | % | 1.4 | 1.4 | 2.8 |
|  | Hole arrangement |  | Lattice | Lattice | Staggered |
| Nonwoven fabric layer B | Composition |  | Polyethylene elastomer | Polyethylene elastomer | Ethylene-1-octene |
|  | Basis weight | g/m² | 30 | 100 | 10 |
|  | Thickness | mm | 0.2 | 0.5 | 0.1 |
|  | Fiber fineness | dtex | 5 | 5 | 0.4 |
| Laminate-bonding of B | Bonding surface |  | Laminate film surface | Laminate fim surface | Laminate film surface |
|  | Adhesive agent |  | Spray bonding | Spray bonding | Spray bonding |
|  | Amount of adhesive agent | g/m² | 4 | 5 | 4 |
| Patch backing | Basis weight | g/m² | 79 | 225 | 39 |
|  | Thickness | mm | 0.42 | 1.02 | 0.22 |
|  | 50% stretch recovery (Machine Direction) | % | 95 | 83 | 98 |
|  | 50% stretch recovery (Transverse Direction) | % | 94 | 83 | 96 |
|  | Moisture permeability | g/m²/24 hr | 4000 | 2800 | 5200 |
| Pasty preparation-laminated surface |  |  | Nonwoven fabric A surface | Nonwoven fabric A surface | Nonwoven fabric A surface |
| Patch appearance | Wrinkle |  | • | • | • |
|  | Stretch or contraction of backing |  | • | • | • |
|  | Exudation |  | • | • | • |
| Evaluation of patch application | Sticky feeling (including damp feeling) |  | • | • | • |
|  | Feeling in application |  | • | ▲ | • |
|  | Pasty preparation retention |  | • | • | • |
|  | Fuzz damage |  | • | • | • |
| Retention of patch function | Moisture retention | % | 48 | 62 | 37 |
|  | Persistence of drug efficacy |  | • | • | • |

|  |  |  | Example 6 | Example 7 | Example 8 |
|---|---|---|---|---|---|
| Nonwoven fabric layer A | Composition |  | Ethylene-1-octene | PET | PP |
|  | Basis weight | g/m² | 30 | 20 | 30 |
|  | Thickness | mm | 0.2 | 0.15 | 0.3 |
|  | Fiber fineness | dtex | 5 | 2 | 3 |
| Laminate film | Composition |  | PP/EPDM | Ethylene-1-octene | Ethylene-1-octene |
|  | Thickness | μm | 15 | 20 | 20 |
|  | Laminate-bonding |  | Laminate | Laminate | Laminate |
| Opening | Method |  | Hot needle processing | Hot needle processing | Hot needle processing |
|  | Through-hole |  | Effective opening | Effective opening | Effective opening |
|  | Opening area | mm² | 0.1 | 0.05 | 0.05 |
|  | Opening ratio | % | 2.8 | 1.4 | 1.4 |
|  | Hole arrangement |  | Staggered | Lattice | Lattice |
| Nonwoven fabric layer B | Composition |  | Ethylene-1-octene | PET | PP |
|  | Basis weight | g/m² | 30 | 20 | 30 |
|  | Thickness | mm | 0.2 | 0.15 | 0.3 |
|  | Fiber fineness | dtex | 5 | 2 | 3 |
| Laminate-bonding of B | Bonding surface |  | Laminate film surface | Laminate film surface | Laminate film surface |
|  | Adhesive agent |  | Spray bonding | Spray bonding | Spray bonding |
|  | Amount of adhesive agent | g/m² | 4 | 5 | 5 |
| Patch backing | Basis weight | g/m² | 79 | 65 | 85 |
|  | Thickness | mm | 0.42 | 0.32 | 0.62 |
|  | 50% stretch recovery (Machine Direction) | % | 98 | 85 | 91 |
|  | 50% stretch recovery (Transverse Direction) | % | 97 | 80 | 90 |
|  | Moisture permeability | g/m²/24 hr | 5000 | 3500 | 3500 |
| Pasty preparation-laminated surface |  |  | Nonwoven fabric A surface | Nonwoven fabric A surface | Nonwoven fabric A surface |
| Patch appearance | Wrinkle |  | • | • | • |
|  | Stretch or contraction of backing |  | • | • | • |
|  | Exudation |  | • | • | • |
| Evaluation of patch application | Sticky feeling (including damp feeling) |  | • | • | • |
|  | Feeling in application |  | • | • | • |

TABLE 1-continued

|  |  |  | Comparative Example 1 | Comparative Example 2 | Comparative Example 3 |
|---|---|---|---|---|---|
| Retention of patch function | Pasty preparation retention | | • | • | • |
| | Fuzz damage | | • | • | • |
| | Moisture retention | % | 40 | 53 | 51 |
| | Persistence of drug efficacy | | • | • | • |

| | | | Comparative Example 1 | Comparative Example 2 | Comparative Example 3 |
|---|---|---|---|---|---|
| Nonwoven fabric layer A | Composition | | Polyethylene elastomer | Polyethylene elastomer | Polyethylene elastomer |
| | Basis weight | g/m$^2$ | 50 | 30 | 30 |
| | Thickness | mm | 0.3 | 0.2 | 0.2 |
| | Fiber fineness | dtex | 5 | 5 | 5 |
| Laminate film | Composition | | Ethylene-1-octene | Ethylene-1-octene | Polyester TPM |
| | Thickness | μm | 20 | 15 | 20 |
| | Laminate-bonding | | Laminate | Laminate | Laminate |
| Opening | Method | | No | Needle punch processing | Hot needle processing |
| | Through-hole | | Ineffective opening | Ineffective opening | Effective opening |
| | Opening area | mm$^2$ | 0 | <0.0005 | 0.05 |
| | Opening ratio | % | 0 | — | 1.4 |
| | Hole arrangement | | — | Lattice | Lattice |
| Nonwoven fabric layer B | Composition | | Polyethylene elastomer | Polyethylene elastomer | Polyethylene elastomer |
| | Basis weight | g/m$^2$ | 45 | 30 | 30 |
| | Thickness | mm | 0.25 | 0.2 | 0.2 |
| | Fiber fineness | ftex | 5 | 5 | 5 |
| Laminate-bonding of B | Bonding surface | | Laminate film surface | Laminate film surface | Laminate film surface |
| | Adhesive agent | | Spray bonding | Spray bonding | Spray bonding |
| | Amount of adhesive agent | g/m$^2$ | 5 | 4 | 4 |
| Patch backing | Basis weight | g/m$^2$ | 120 | 79 | 84 |
| | Thickness | mm | 0.57 | 0.42 | 0.42 |
| | 50% stretch recovery (Machine Direction) | % | 91 | 95 | 98 |
| | 50% stretch recovery (Transverse Direction) | % | 91 | 94 | 97 |
| | Moisture permeability | g/m$^2$/24 hr | 21 | 210 | 3800 |
| Pasty preparation-laminated surface | | | Nonwoven fabric A surface | Nonwoven fabric A surface | Nonwoven fabric A surface |
| Patch appearance | Wrinkle | | • | • | • |
| | Stretch or contraction of backing | | • | • | • |
| | Exudation | | • | • | • |
| Evaluation of patch application | Sticky feeling (including damp feeling) | | x | x | • |
| | Feeling in application | | • | • | • |
| | Pasty preparation retention | | • | • | • |
| | Fuzz damage | | • | • | • |
| Retention of patch function | Moisture retention | % | 96 | 93 | 53 |
| | Persistence of drug efficacy | | • | • | • |

| | | | Comparative Example 4 | Comparative Example 5 | Comparative Example 6 |
|---|---|---|---|---|---|
| Nonwoven fabric layer A | Composition | | Polyethylene elastomer | Polyethylene elastomer | Polyethylene elastomer |
| | Basis weight | g/m$^2$ | 30 | 50 | 50 |
| | Thickness | mm | 0.2 | 0.3 | 0.3 |
| | Fiber fineness | dtex | 5 | 5 | 5 |
| Laminate film | Composition | | No | Ethylene-1-octene | Ethylene-1-octene |
| | Thickness | μm | — | 20 | 20 |
| | Laminate-bonding | | No | Laminate | Laminate |
| Opening | Method | | No | No | Hot needle processing |
| | Through-hole | | No | Ineffective opening | Effective opening |
| | Opening area | mm$^2$ | — | 0 | 0.05 |
| | Opening ratio | % | — | 0 | 1.4 |
| | Hole arrangement | | — | — | Lattice |
| Nonwoven fabric layer B | Composition | | Polyethylene elastomer | No | No |
| | Basis weight | g/m$^2$ | 30 | — | — |
| | Thickness | mm | 0.2 | — | — |
| | Fiber fineness | ftex | 5 | — | — |
| Laminate-bonding of B | Bonding surface | | Nonwoven fabric A surface | No | No |
| | Adhesive agent | | Spray bonding | — | — |
| | Amount of adhesive agent | g/m$^2$ | 10 | — | — |
| Patch backing | Basis weight | g/m$^2$ | 70 | 70 | 70 |
| | Thickness | mm | 0.4 | 0.32 | 0.32 |
| | 50% stretch recovery (Machine Direction) | % | 84 | 95 | 95 |
| | 50% stretch recovery (Transverse Direction) | % | 82 | 94 | 94 |
| | Moisture permeability | g/m$^2$/24 hr | 8200 | 22 | 4500 |

TABLE 1-continued

| | | | | | |
|---|---|---|---|---|---|
| Pasty preparation-laminated surface | | | Nonwoven fabric A surface | Laminate film surface | Laminate film surface |
| Patch appearance | Wrinkle | | • | • | • |
| | Stretch or contraction of backing | | | • | • |
| | Exudation | | x | • | • |
| Evaluation of patch application | Sticky feeling (including damp feeling) | | • | x | • |
| | Feeling in application | | • | • | • |
| | Pasty preparation retention | | • | x | x |
| | Fuzz damage | | x | • | • |
| Retention of patch function | Moisture retention | % | 11 | 96 | 44 |
| | Persistence of drug efficacy | | x | • | • |

| | | | Comparative Example 7 | Comparative Example 8 | Comparative Example 9 |
|---|---|---|---|---|---|
| Nonwoven fabric layer A | Composition | | Polyethylene elastomer | Polyethylene elastomer | Polyethylene elastomer |
| | Basis weight | g/m² | 50 | 50 | 50 |
| | Thickness | mm | 0.3 | 0.3 | 0.3 |
| | Fiber fineness | dtex | 5 | 5 | 5 |
| Laminate film | Composition | | Ethylene-1-octene | Ethylene-1-octene | PP |
| | Thickness | μm | 20 | 20 | 20 |
| | Laminate-bonding | | Laminate | Laminate | Laminate |
| Opening | Method | | No | Hot needle processing | Hot needle processing |
| | Through-hole | | Ineffective opening | Effective opening | Effective opening |
| | Opening area | mm² | 0 | 0.05 | 0.05 |
| | Opening ratio | % | 0 | 1.4 | 1.4 |
| | Hole arrangement | | — | Lattice | Lattice |
| Nonwoven fabric layer B | Composition | | No | No | Polyethylene elastomer |
| | Basis weight | g/m² | — | — | 45 |
| | Thickness | mm | — | — | 0.25 |
| | Fiber fineness | ftex | — | — | 5 |
| Laminate-bonding of B | Bonding surface | | No | No | Laminate film surface |
| | Adhesive agent | | — | — | Spray bonding |
| | Amount of adhesive agent | g/m² | — | — | 5 |
| Patch backing | Basis weight | g/m² | 70 | 70 | 120 |
| | Thickness | mm | 0.32 | 0.32 | 0.57 |
| | 50% stretch recovery (Machine Direction) | % | 95 | 95 | 45 |
| | 50% stretch recovery (Transverse Direction) | % | 94 | 94 | 42 |
| | Moisture permeability | g/m²/24 hr | 22 | 4500 | 3600 |
| Pasty preparation-laminated surface | | | Nonwoven fabric A surface | Nonwoven fabric A surface | Nonwoven fabric A surface |
| Patch appearance | Wrinkle | | • | • | • |
| | Stretch or contraction of backing | | • | • | x |
| | Exudation | | • | • | • |
| Evaluation of patch application | Sticky feeling (including damp feeling) | | x | • | • |
| | Feeling in application | | x | x | x |
| | Pasty preparation retention | | • | • | x |
| | Fuzz damage | | x | x | x |
| Retention of patch function | Moisture retention | % | 96 | 45 | 53 |
| | Persistence of drug efficacy | | • | • | • |

| | | | Comparative Example 10 | Comparative Example 11 | Comparative Example 12 |
|---|---|---|---|---|---|
| Nonwoven fabric layer A | Composition | | Polyethylene elastomer | Polyethylene elastomer | Polyethylene elastomer |
| | Basis weight | g/m² | 30 | 30 | 30 |
| | Thickness | mm | 0.2 | 0.2 | 0.3 |
| | Fiber fineness | dtex | 5 | 5 | 5 |
| Laminate film | Composition | | Ethylene-1-octene | Ethylene-1-octene | Ethylene-1-octene |
| | Thickness | μm | 15 | 15 | 20 |
| | Laminate-bonding | | Laminate | Laminate | Laminate |
| Opening | Method | | Hot needle processing | Hot needle processing | Hot needle processing |
| | Through-hole | | Effective opening | Effective opening | Effective opening |
| | Opening area | mm² | 0.05 | 3 | 0.2 |
| | Opening ratio | % | 0.5 | 15 | 1.4 |
| | Hole arrangement | | Staggered | Staggered | Lattice |
| Nonwoven fabric layer B | Composition | | Polyethylene elastomer | Polyethylene elastomer | Polyethylene elastomer |
| | Basis weight | g/m² | 30 | 30 | 45 |
| | Thickness | mm | 0.2 | 0.2 | 0.25 |
| | Fiber fineness | ftex | 5 | 5 | 5 |
| Laminate-bonding of B | Bonding surface | | Laminate film surface | Laminate film surface | Laminate film surface |
| | Adhesive agent | | Spray bonding | Spray bonding | Spray bonding |
| | Amount of adhesive agent | g/m² | 4 | 4 | 5 |

TABLE 1-continued

| | | | | | |
|---|---|---|---|---|---|
| Patch backing | Basis weight | g/m² | 79 | 79 | 120 |
| | Thickness | mm | 0.42 | 0.42 | 0.58 |
| | 50% stretch recovery (Machine Direction) | % | 95 | 95 | 89 |
| | 50% stretch recovery (Transverse Direction) | % | 94 | 94 | 89 |
| | Moisture permeability | g/m²·24 hr | 960 | 6800 | 6100 |
| Pasty preparation-laminated surface | | | Nonwoven fabric A surface | Nonwoven fabric A surface | Nonwoven fabric A surface |
| Patch appearance | Wrinkle | | • | • | • |
| | Stretch or contraction of backing | | • | • | • |
| | Exudation | | • | x | x |
| Evaluation of patch application | Sticky feeling (including damp feeling) | | x | • | • |
| | Feeling in application | | • | • | • |
| | Pasty preparation retention | | • | • | • |
| | Fuzz damage | | • | • | • |
| Retention of patch function | Moisture retention | % | 89 | 17 | 25 |
| | Persistence of drug efficacy | | • | x | x |

INDUSTRIAL APPLICABILITY

The patch using the patch backing for a water-based pasty preparation of the present invention has an excellent pasty preparation retention property and an excellent moisture retention property, improves the persistence of drug efficacy by inhibiting the sublimation of the drug, gives no restrained feeling due to the thin thickness and the excellent elasticity, hardly gives a sticky feeling due to the optimized moisture permeability, and gives an excellent feeling in application. The present invention can provide the patch backing which is the best for the patch for a water-based pasty preparation.

The invention claimed is:

1. A patch backing for a water-based pasty preparation consisting of a laminate,
   wherein the laminate consists of a film layer having through-holes which is laminated between a nonwoven fabric layer A and a nonwoven fabric layer B,
   wherein the through-holes extend from the nonwoven fabric layer A through the film layer,
   wherein the through-holes are not formed in the nonwoven fabric layer B,
   wherein the film layer consists of a resin comprising an olefin elastomer,
   wherein an area per through-hole is 0.02-0.18 mm²,
   wherein an opening ratio of the through-hole is 1-10%,
   wherein a moisture permeability of the patch backing is 1000-5500 g/m²·24 hours, and
   wherein the patch backing has a thickness of 0.3-0.8 mm, and
   wherein the film layer has a thickness of 5-50 μm.

2. The patch backing for a water-based pasty preparation according to claim 1,
   wherein the patch backing has a 50% stretch recovery ratio of 70%-100%, a basis weight of 50-140 g/m², and a thickness of 0.3-0.5 mm.

3. The patch backing for a water-based pasty preparation according to claim 1,
   wherein the nonwoven fabric layer A and the nonwoven fabric layer B consist of an olefin resin.

4. The patch backing for a water-based pasty preparation according to claim 1,
   wherein the nonwoven fabric layer A and the nonwoven fabric layer B consist of a resin containing an olefin elastomer.

5. The patch backing for a water-based pasty preparation according to claim 2,
   wherein the nonwoven fabric layer A and the nonwoven fabric layer B consist of an olefin resin.

6. The patch backing for a water-based pasty preparation according to claim 2,
   wherein the nonwoven fabric layer A and the nonwoven fabric layer B consist of a resin containing an olefin elastomer.

7. The patch backing for a water-based pasty preparation according to claim 1,
   wherein at least one of the nonwoven fabric layer A and the nonwoven fabric layer B consists of a resin comprising an olefin elastomer.

8. The patch backing for a water-based pasty preparation according to claim 1,
   wherein the olefin elastomer is at least one selected from the group consisting of ethylene/propylene copolymer, ethylene/1-butene copolymer, propylene/1-butene copolymer, and ethylene/1-octene copolymer.

9. The patch backing for a water-based pasty preparation according to claim 3,
   wherein the olefin resin comprises at least one of polyethylene, polypropylene, polybutene, ethylene-α-olefin copolymer, propylene-α-olefin copolymer, and ethylene vinyl alcohol.

10. The patch backing for a water-based pasty preparation according to claim 8,
    wherein the olefin elastomer is ethylene/1-octene copolymer.

11. The patch backing for a water-based pasty preparation according to claim 1,
    wherein the resin comprise from 5% to 100% by weight of the olefin elastomer.

12. The patch backing for a water-based pasty preparation according to claim 1,
    wherein the area per through-hole is from about 0.05 mm² to about 0.17 mm².

13. The patch backing for a water-based pasty preparation according to claim 1,
    wherein the opening ratio of the through-hole is from about 1% to about 8%.

14. The patch backing for a water-based pasty preparation according to claim 1, wherein each of the nonwoven fabric layers A, B has a basis weight of 15-80 g/m², so that the patch backing has a basis weight of 50-140 g/m², and wherein the basis weight of the nonwoven fabric layer B is higher than the basis weight of the nonwoven fabric layer A.

\* \* \* \* \*